United States Patent [19]

Ward et al.

[11] Patent Number: 4,950,683
[45] Date of Patent: Aug. 21, 1990

[54] MACROLIDE ANTIBIOTICS

[75] Inventors: John B. Ward, Bushey; Hazel M. Noble, Burnham; Neil Porter, Pinner; Richard A. Fletton, Ruislip; David Noble, Burnham; Derek R. Sutherland, Chalfont St. Giles; Michael V. J. Ramsay, South Harrow, all of England

[73] Assignee: American Cyanamid Company, Stamford, Conn.

[21] Appl. No.: 119,345

[22] Filed: Nov. 10, 1987

Related U.S. Application Data

[63] Continuation of Ser. No. 906,525, Sep. 12, 1986, abandoned.

[30] Foreign Application Priority Data

Sep. 13, 1985 [GB] United Kingdom ............... 8522692
Sep. 13, 1985 [GB] United Kingdom ............... 8522695

[51] Int. Cl.$^5$ ............... A61K 31/365; C07D 315/00
[52] U.S. Cl. ............... 514/450; 549/264
[58] Field of Search ............... 549/264; 514/450

[56] References Cited

U.S. PATENT DOCUMENTS

| Re. 32,034 | 11/1985 | Chabala et al. | 549/264 |
| 4,201,861 | 5/1980 | Mrozik et al. | 536/7.1 |
| 4,328,335 | 5/1982 | Mrozik | 536/7.1 |
| 4,378,353 | 3/1983 | Goegelman et al. | 435/119 |
| 4,423,209 | 12/1983 | Mrozik | 549/264 |
| 4,587,247 | 5/1986 | Linn et al. | 549/264 |

FOREIGN PATENT DOCUMENTS

| 170006 | 2/1986 | European Pat. Off. | |
| 16894 | 1/1984 | Japan | 549/264 |
| 20284 | 2/1984 | Japan | 549/264 |

OTHER PUBLICATIONS

H. Gerlach et al., Helv. Chim. Acta, vol. 55 (1972), pp. 2277–2286, 2962–2964.

H. Gerlach et al., Jour. Chem. Soc., Chem. Comm. (1972), pp. 1215–1216.
E. M. Burgess et al., J. Org. Chem., vol. 38(1) (1973), pp. 26–31.
H. J. Eli Loewenthal et al. Chem. Soc. Jour. Perkin Transactions I, vol. 21, (1975), pp. 2149–2157.
Leo A. Paquette et al., J. Org. Chem., vol. 42(16), Aug. 1977, pp. 2659–2665.
W. H. Rastetter et al., J. Org. Chem. (1980) vol. 45, pp. 3149–3155.

Primary Examiner—Richard L. Raymond
Assistant Examiner—Amelia A. Owens
Attorney, Agent, or Firm—Bacon & Thomas

[57] ABSTRACT

Compounds are described of formula (I)

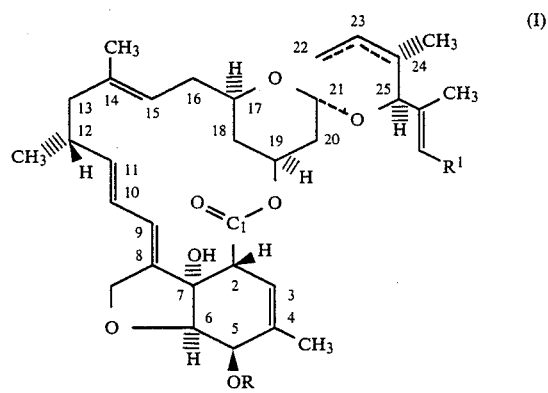

and salts thereof, wherein OR is a hydroxyl group or a substituted hydroxyl group having up to 25 carbon atoms, $R^1$ represents a methyl, ethyl or isopropyl group and the broken line represents a double bond at the 22,23-position or at the 23,24-position.

These compounds may be used for controlling insect, acarine, nematode or other pests.

8 Claims, No Drawings

MACROLIDE ANTIBIOTICS

This application is a continuation, of application Ser. No. 906,525, filed Sept. 12, 1986, now abandoned.

This invention relates to novel antibiotic compounds and to processes for their preparation.

In our United Kingdom Patent Specification No. 2166436A we describe the production of Antibiotics S541 which may be isolated from the fermentation products of a novel *Streptomyces* sp.

We have now found a further group of compounds with antibiotic activity which may be prepared by chemical modification of Antibiotics S541. The novel compounds of the invention have antibiotic activity and/or are of use as intermediates in the preparation of other active compounds.

Thus, in one aspect, the invention particularly provides the compounds of formula (I)

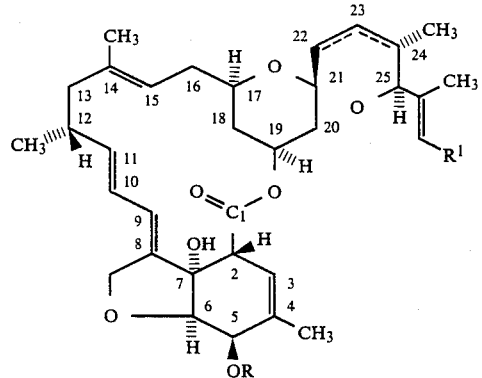

and salts thereof, wherein OR is a hydroxyl group or a substituted hydroxyl group having up to 25 carbon atoms and $R^1$ represents a methyl, ethyl or isopropyl group. The broken line in the compounds of formula (I) means that there is a double bond at the 22,23-position or at the 23,24-position.

Hence the present invention covers compounds of formula (IA) and (IB)

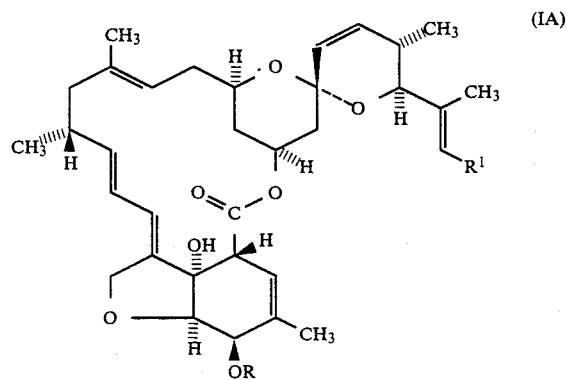

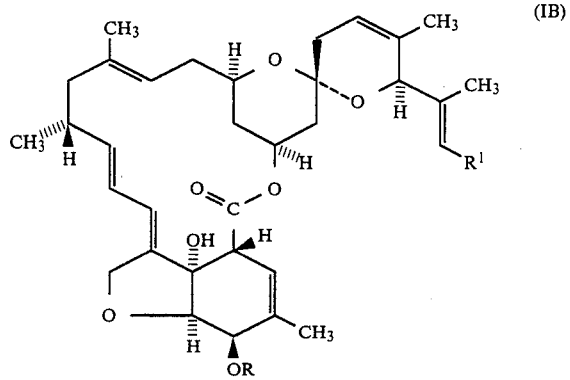

(wherein OR and $R^1$ are as defined above).

When the compounds of formula (I) are to be used as intermediates —OR will often be a protected hydroxy group and the invention particularly includes such protected compounds.

When the groups OR in compounds of formula (I) is a substituted hydroxyl group it may represent an acyloxy group [e.g. a group of the formula —$OCOR^2$, —$OCO_2R^2$ or —$OCSOR^2$ (where $R^2$ is an aliphatic, araliphatic or aromatic group, for example an alkyl, alkenyl, alkynyl, cycloalkyl, aralkyl or aryl group)], a formyloxy group, a group —$OR^3$ (where $R^3$ is as defined above for $R^2$), a group —$OSO_2R^4$ (where $R^4$ is a $C_{1-4}$ alkyl or $C_{6-10}$ aryl group), a silyloxy group, a cyclic or acyclic acetaloxy group, a group $OCO(CH_2)_nCO_2R^5$ (where $R^5$ is a hydrogen atom or a group as defined for $R^2$ above and n represents zero, 1 or 2) or a group $OCONR^6R^7$ (where $R^6$ and $R^7$ may each independently represent a hydrogen atom or a $C_{1-4}$ alkyl group e.g. methyl).

Where $R^2$ or $R^3$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^2$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^3$ is a substituted alkyl group it may be substituted by a cycloalkyl e.g. cyclopropyl group.

Where $R^2$ or $R^3$ are alkenyl or alkynyl groups, they may be for example $C_{2-8}$ alkenyl, e.g. allyl, or $C_{2-8}$ alkynyl groups.

Where $R^2$ or $R^3$ are cycloalkyl groups, they may be for example $C_{3-12}$ cycloalkyl, such as $C_{3-7}$ cycloalkyl, e.g. cyclopentyl groups.

Where $R^2$ or $R^3$ are aralkyl groups, they preferably have 1 to 6 carbon atoms in the alkyl moiety and the aryl group(s) may be carbocyclic or heterocyclic and preferably contain 4–15 carbon atoms e.g. phenyl. Examples of such groups include phen$C_{1-6}$ alkyl, e.g. benzyl groups.

Where $R^2$ or $R^3$ are aryl groups, they may be carbocyclic or heterocyclic and preferably have 4–15 carbon atoms, and may be for example a phenyl group.

When —OR is a group —$OSO_2R^4$, it may be for example a methylsulphonyloxy or p-toluenesulphonyloxy group.

Where —OR represents a cyclic acetaloxy group, it may for example have 5–7 ring members and may be for example a tetrahydropyranyloxy group.

When —OR represents a silyloxy group or $R^2$ contains a silyloxy substituent, the silyl group may carry three groups which may be the same or different, selected from alkyl, alkenyl, alkoxy, cycloalkyl, aralkyl, aryl and aryloxy groups. Such groups may be as defined above for $R^2$ and particularly include methyl, t-butyl and phenyl groups. Particular examples of such silyloxy groups are trimethylsilyloxy and t-butyldimethylsilyloxy.

Where OR represents a group $OCO(CH_2)_nCO_2R^5$, it may for example be a group $OCOCO_2R^5$ or $OCOCH_2CH_2CO_2R^5$ where $R^5$ represents a hydrogen atom or a $C_{1-4}$ alkyl (e.g. methyl or ethyl) group.

Salts that may be formed with compounds of formula (I) containing an acidic group include alkali metal salts such as sodium and potassium salts.

In the compounds of formula (I), the group $R^1$ is preferably an isopropyl group.

Compounds of formula (I) in which the group OR is a methoxycarbonyloxy or, especially, an acetoxy or hydroxy group are also preferred. In general, compounds of formula (I) in which OR is a hydroxy group are particularly preferred.

The 23-desoxy $\Delta^{22}$ derivatives of formula (IA) are generally preferred.

A particularly important compound according to the invention is that of formula (IA) in which $R^1$ is an isopropyl group and OR is a hydroxy group.

As indicated previously, the compounds according to the invention may be of use as antibiotics and/or as intermediates for the preparation of other active compounds. When the compounds of the invention are to be used as intermediates, the —OR group may be a protected hydroxyl group. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Synthesis" by Theodora W. Greene. (Wiley-Interscience, New York 1981) and "Protective Groups in Organic Chemistry" by J. F. W. McOmie (Plenum Press, London, 1973). Examples of OR protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups, such as acetoxy, may serve as protected hydroxyl groups, but may also be present in final active compounds.

Compounds of the invention have antibiotic activity e.g. antihelminthic activity, for example against nematodes, and in particular, anti-endoparasitic and anti-ectoparasitic activity.

Ectoparasites and endoparasites infect humans and a variety of animals and are particularly prevalent in farm animals such as pigs, sheep, cattle, goats and poultry, horses and domestic animals such as dogs and cats. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Uncinaria and Wuchareria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Demallenia, Dermatobia, Gastrophilus, Haematobia, Haematopinus, Haemophysalis, Hyalomma, Hyperderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. In particular, we have found that compounds of the invention are active against parasitic nematodes such as *Nematospiroides dubius* and *Nippostrongylus braziliensis*.

The compounds of the invention are therefore of use in treating animals and humans with endoparasitic and/or ectoparasitic infections.

The antibiotic activity of compounds of the invention may, for example, be demonstrated by their activity in vitro against free living nematodes e.g. *Caenorhabiditis elegans*.

Furthermore, compounds of the invention are of use as anti-fungals, for example, against strains of Candida sp. such as *Candida albicans* and *Candida glabrata* and against yeast such as *Saccharomyces carlsbergensis*.

Compounds of the invention are also of use in combating insect, acarine and nematode pests in agriculture, horticulture, forestry, public health and stored products. Pests of soil and plant crops, including cereals (e.g. wheat, barley, maize and rice) vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti.*

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or to the pests themselves or a locus thereof.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in veterinary or human medicine by injection and may be presented in unit dose form, in ampoules, or other unit-dose containers, or in multi-dose containers, if necessary with an added preservative. The compositions for injection may be in the form of suspensions, solutions, or emulsions in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intrammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcellulose); fillers (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be included.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agents or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients.

The total daily dosages of compounds of the invention employed in both veterinary and human medicine will suitably be in the range 1–2000 μg/kg bodyweight, preferably from 50–1000 μg/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in formulations such as dusts, granulates and powders may be selected from for example natural mineral fillers, such as diatomite, talc, kaolinite, montmorillonite pyrophyllite or attapulgite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, ester, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The compounds of the invention will be prepared by the processes discussed below. In preparing compounds of formula (I) in which OR is a hydroxy group it may be necessary to protect the hydroxyl group at the 5-position in the starting material prior to effecting the reaction described. In such cases it may then be necessary to deprotect the same hydroxyl group once the reaction has occurred to obtain the desired compound of the invention. Conventional protection and deprotection methods may be used, for example as described in the aforementioned books by Greene and McOmie.

Thus, for example, an acyl group such as an acetyl group may be removed by basic hydrolysis e.g. using sodium or potassium hydroxide in aqueous alcohol or acidic hydrolysis e.g. using concentrated sulphuric acid in ethanol. Acetal groups such as tetrahydropyranyl may be removed for example, using acid hydrolysis (using an acid such as acetic or trifluoroacetic acid or a dilute mineral acid). Silyl groups may be removed using fluoride ions (e.g. from a tetraalkylammonium fluoride such as tetra-n-butylammonium fluoride), hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the the presence of a thiol (e.g. ethanethiol) in a suitable solvent such as dichloromethane at e.g. room temperature.

According to one general process the compounds of the invention may be prepared by elimination.

Thus, for example, according to a further aspect of the invention we provide a process for the preparation of a compound of formula (I) which comprises elimination of HL from a compound of formula (II)

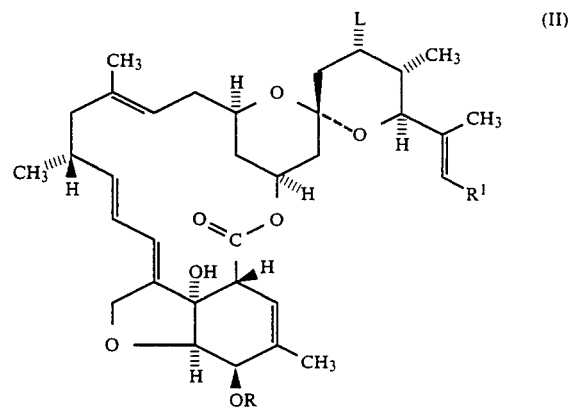

(where L is an eliminatable group, such as a group —$OR^a$, where $OR^a$ is a hydroxy group or an acyloxy group, e.g. a group —$OCSOR^2$ as defined for formula (I)) followed if desired by removal of any group R (where R is other than —H) to form a compound in which R is —H and optionally subsequently introducing a desired group R (where R is other than —H) by reaction of the resulting compound in which R is H with a reagent serving to introduce said group.

The elimination reaction to yield a compound of formula (I) may be effected using conventional techniques.

Thus, in one embodiment of the process, compound of formula (IA) may be prepared from compounds of formula (II) in which the group L is acyloxy, e.g.

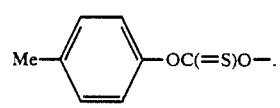

The elimination may be effected by pyrolysis, for example at a temperature of 150°–300° C., preferably 200°–250° C., either in a suitable solvent such as halogenated hydrocarbon, e.g. trichlorobenzene or in the absence of solvent using an inert diluent such as sand.

In another embodiment of the process, compounds of formula (IB) may be prepared from compounds of formula (II) in which the group L is hydroxy. The elimination may be effected using a reagent such as diethylaminosulphur trifluoride in a solvent such as dichloromethane at a low temperature e.g. −70° C. Alternatively, the elimination may be performed using a reagent such as $(CH_3CH_2)_3NSO_2NCO_2CH_3$ (Burgess et al., J. Org. Chem., 1973, 38, 26) in a solvent such as toluene.

The conversion of the —OR group of compounds of the invention (in which R is other than —H) into a hydroxyl group is a step which will usually be carried out in the context of removing a protecting group such as referred to above.

According to a further aspect of the invention we provide a further process for the preparation of compounds of formula (I) in which OR is a substituted hydroxyl group which comprises reacting a compound of formula (I) (where $R^1$ is as defined previously and OR is a hydroxyl group) with a reagent serving to convert a hydroxyl group into a substituted hydroxyl group.

The reaction will in general be an acylation, formylation, sulphonylation, etherification, silylation or acetal formation.

Thus, for example, acylation may be effected using an acylating agent such as an acid of formula $R^2COOH$ or a reactive derivative thereof, such as an acid halide (e.g. acid chloride), anhydride or activated ester, or a reactive derivative of a carbonic acid $R^2OCOOH$ or thiocarbonic acid $R^2OCSOH$.

Acylations employing acid halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing acids are desirably conducted in the presence of a condensing agent, for example a carbodiimide such as N,N'-dicyclohexylcarbodiimide or N-ethyl-N'γ-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in aqueous or non-aqueous reaction media, conveniently at a temperature in the range −20° to +100° C., e.g. −10° to +50° C.

Formylation may be effected using an activated derivative of formic acid e.g. N-formyl imidazole or formic acetic anhydride under standard reaction conditions.

Sulphonylation may be effected with a reactive derivative of a sulphonic acid $R^4SO_3H$ such as a sulphonyl halide, for example a chloride $R^4SO_2Cl$ or a sulphonic anhydride. The sulphonylation is preferably effected in the presence of a suitable acid binding agent as described above.

Etherification may be effected using a reagent of formula $R^3Y$ (where $R^3$ is as previously defined and Y represents a leaving group such as a chlorine, bromine or iodine atom, or a hydrocarbylsulphonyloxy group e.g. mesyloxy or tosyloxy, or a haloalkanoyloxy group e.g. dichloroacetoxy).

The reaction may be carried out by initial formation of a magnesium alkoxide using a Grignard reagent such as a methylmagnesium halide e.g. methylmagnesium iodide or using a trialkylsilylmethylmagnesium halide e.g. trimethylsilylmethylmagnesium chloride followed by treatment with the reagent $R^3Y$.

Alternatively, the reaction may be effected in the presence of a silver salt such as silver oxide, silver perchlorate, silver carbonate or silver salicylate or mixtures thereof, and this system may be particularly appropriate when the etherification is carried out using a reagent $R^3Y$ wherein Y is a halogen atom.

Etherification may conveniently be effected in a solvent such as an ether e.g. diethyl ether.

Acetal formation may be carried out by reaction with a cyclic or acyclic vinyl ether. This method is especially useful for production of tetrahydropyranyl ethers, using dihydropyran as reagent, or 1-alkoxyalkyl ethers such as 1-ethoxyalkyl ether, using an alkyl vinyl ether as reagent. The reaction is desirably carried out in the presence of a strong acid catalyst, for example a mineral acid such as sulphuric acid, or an organic sulphonic acid such as p-toluene sulphonic acid, in a non-hydroxylic, substantially water-free solvent.

Solvents which may be employed in the above reactions include ketones (e.g. acetone), amides (e.g. N,N-dimethylformamide, N,N-dimethylacetamide or hexamethylphosphoramide), ethers (e.g. cyclic ethers such as tetrahydrofuran or dioxan, and acyclic ethers such as dimethoxyethane or diethylether), nitriles (e.g. acetonitrile), hydrocarbons such as halogenated hydrocarbons (e.g. methylene chloride), and esters such as ethyl acetate, as well as mixtures of two or more such solvents.

Silylation may be effected by reaction with a silyl halide (e.g. chloride), advantageously in the presence of a base such as imidazole triethylamine or pyridine, using a solvent such as dimethylformamide.

The intermediates of formula (II) in which OR is a hydroxy or methoxy group and L is a hydroxy group may be obtained using the fermentation and isolation methods described in UK Patent Specification No. 2166436A. Other intermediates of formula (II) may be prepared from these compounds using methods described above for the preparation of compounds of formula (I) in which OR is a substituted hydroxyl group. Thus, for example, a compound of formula (II) in which L is an acyloxy group may be prepared from the corresponding compound in which L is OH by acylation according to the method described above for the preparation of compounds of formula (I).

The invention is further illustrated by the following Preparations and Examples wherein the intermediate of formula (II) in which $R^1$ is an isopropyl group, OR is a hydroxy group and L is referred to as "Factor A". All temperatures are in °C.

PREPARATION 1

5-Acetoxy Factor A

Factor A (3.0 g) in pyridine (20 ml) at −5° was treated with acetic anhydride (8 ml) and the resulting solution left at 3° for 20 hr. Benzene (100 ml) was added and the solution concentrated in vacuo. The residual oil was chromatographed over silica using dichloromethane:acetone (40:1) as eluent to give the 5-acetoxy of Factor A (2.06 g), containing 10% 5,23-diacetoxy Factor A. The compounds were separated by reverse-phase preparative hplc to give the title compound (79% recovery), $\lambda_{max}$ (EtOH) 244.5 nm ($E_1^1$462), $\delta$(CDCl$_3$) includes 2.14 (s; 3H), m/z includes 654, 594 and 576.

PREPARATION 2

5-Phenoxyacetyl Factor A

Factor A (2.0 g) in dichloromethane (25 ml) and pyridine (0.35 ml) at 0° was treated with a solution of phenoxyacetyl chloride (0.5 ml) in dichloromethane. After 18 hr at 3° the solution was treated with pyridine (1.0 ml) and with phenoxyacetyl chloride (1.0 ml) in dichloro methane (5 ml). The solution was stirred at 0° to 5° for 30 min before being poured into ice-water (100 ml). Ether (100 ml) was added and the mixture stirred for 20 min. The aqueous layer was extracted with ether (100 ml). The ether layers were combined, washed successively with water (100 ml) and brine (100 ml), dried and evaporated. The residue (2.3 g) was purified by silica chromatography using dichloromethane:acetone (40:1) to give the 5-phenoxyacetyl of Factor A containing 5,23-diphenoxyacetyl Factor A (1.8 g, monoacyl:diacyl=6:1). The compounds were separated by reverse-phase preparative hplc to give the title compound, $\delta$(CDCl$_3$) include 6.8 to 7.4 (m; 5H) and 4.66 (s; 2H), m/z include 746, 728, 710, 594 and 576.

PREPARATION 3

5-Phenoxyacetyl,23-p-tolyloxythiocarbonyloxy Factor A

The product of Preparation 2 (747 mg) in dichloromethane (10 ml) at 0° under nitrogen was treated with pyridine (0.81 ml) and then with p-tolylchlorothionoformate (0.75 g) in dichloromethane (2 ml). The dark solution was stirred for 15 min at 0° and then for 22 hr without cooling. The mixture was poured into cold water (100 ml) and brine (30 ml), and extracted with ether (3×100 ml). The combined ether layers were washed with water (150 ml) and brine (150 ml), dried and evaporated. The residue was purified by silica column chromatography and reverse-phase preparative hplc to give the title compound (430 mg), $\delta$(CDCl$_3$) include 3.34 (m; 1H), 3.58 (m; 1H), 3.97 (d10; 1H), 4.72 (s; 2H), 5.4 (m; 1H), 5.59 (d6; 1H) and 6.9 to 7.4 (m; 9H), m/z include 728, 616, 576, 466, 464, 448, 354, 297, 247, 219 and 151.

PREPARATION 4

5-Acetoxy,23-p-tolyloxythiocarbonyloxy Factor A

A solution of the product of Preparation 1 (1.112 g) in dry dichloromethane (12 ml) and dry pyridine (1.37 ml, 1.34 g, 16.9 mmol, 10 mol eq) was treated, in an atmosphere of nitrogen with p-tolylchlorothionoformate (1.05 ml, 1.27 g, 6.79 mmol, 4 mol eq), added in one portion. After 9 h at 21° the red/brown solution was poured into dichloromethane (80 ml) and washed successively with 2N hydrochloric acid (2×50 ml), saturated aqueous sodium bicarbonate (2×50 ml), water (60 ml) and brine. The organic phase was stirred for 5 min with charcoal and was then dried and evaporated to leave a gum (1.862 g). A solution of the gum in hexane:ethyl acetate=4:1 was applied to a column of Merck Kieselgel 60, 15μ silica (200 g). Elution of this column under high pressure (8 bar), with the same solvent system afforded the title compound as a yellow foam (852 mg). $[\alpha]_D^{21}$ +170.2 (c 0.3, CHCl$_3$), $\lambda_{max}^{EtOH}$ 239 (34,000) and 244.5 nm ($\epsilon_{max}$ 35,000); $\nu_{max}$ (CHBr$_3$) 3320 to 3620 (br OH), 1730 and 1710 cm$^{-1}$ (br ester); $\delta$(CDCl$_3$) includes 0.81 (d, 6 Hz; 3H), 0.95 (d, 6 Hz; 3H), 1.00 (d, 6 Hz; 3H), 1.05 (d, 6 Hz; 3H), 1.54 (s; 3H) 1.62 (s; 3H), 1.76 (s; 3H), 2.16 (s; 3H), 2.36 (s; 3H) 3.34 (m; 1H), 3.96 (d, 10 Hz; 1H), 4.06 (d, 6 Hz; 1H), 5.5 to 5.6 (m; 2H), 6.99 (d, 7 Hz; 2H) and 7.20 (d, 7 Hz; 2H).

PREPARATION 5

5-Acetoxy,23-phenyloxythiocarbonyloxy Factor A

Phenyl chlorothionoformate (1.90 ml) was added to a stirred solution of the product of Preparation 1 (3.0 g) and pyridine (3.70 ml) in dichloromethane (30 ml) at room temperature, under an atmosphere of nitrogen. After stirring for 16 h the dark brown reaction mixture was diluted with ethyl acetate (250 ml), washed with 2M hydrochloric acid (2×250 ml), saturated sodium bicarbonate solution (250 ml) and brine (250 ml), and dried (Na$_2$SO$_4$). The solvent was evaporated and the residue purified by flash chromatography (250 g silica gel, Merck 9385). Elution with ethyl acetate:light petroleum (1:4→1:3) afforded the title compound as an orange foam (2.68 g) $\lambda_{max}$ (EtOH) 235.6 nm ($\epsilon$34,500), 243.4 nm ($\epsilon$36,200); $\nu_{max}$ 3470 (OH), 1730, 1710 cm$^{-1}$ (esters); $\delta$(CDCl$_3$) values include 7.42 (2H, t, J 8 Hz), 7.29 (1H,t,J 8 Hz), 7.12 (2H,d, J 8 Hz) 4.97 (1H,m), 3.96 (1H,d,J 10 Hz), 3.34 (1H,m) 2.17 (3H,s), 1.38 (1H,t,J 12 Hz).

EXAMPLE 1

23-Desoxy $\Delta^{22}$ Factor A

A solution of the product of Preparation 3 (0.4 g) in 1,2,4-trichlorobenzene (10 ml) was heated at 200°–210° for 2.5 hr. The solvent was removed in vacuo and the residue purified by preparative reverse-phase hplc to give 5-phenoxyacetyl 23-desoxy $\Delta^{22}$ Factor A. A portion of the latter compound (25 mg) in methanol (5 ml) at 0° was added to a stirred solution of methanol (15 ml) saturated with ammonia at 0°. The solution was stirred at 0°–5° for 2.5 hr, before being evaporated to dryness. The residue was purified by preparative tlc over silica using dichloromethane:acetone (10:1) as eluent, to give the title compound as a colourless solid (15 mg), $\delta$(CDCl$_3$) include 0.83 (d7; 3H), 0.94 (d7; 3H), 0.98 (d7; 6H), 1.02 (d6; 3H), 1.52 (s; 3H), 1.66 (s; 3H), 1.86 (s; 3H), 3.27 (m; 1H), 3.71 (d10; 1H), 3.95 (d6; 1H), 4.28 (t6; 1H), 5.20 (d9; 1H), 5.56 (dd10, 2; 1H) and 5.6–5.9 (m; 3H), m/z include 594, 576, 482, 466, 448, 354, 314, 297, 247, 219 and 151.

EXAMPLE 2

5-Acetoxy,23-desoxy $\Delta^{22}$ Factor A

The product of Preparation 4 (200 mg) was immersed, under an atmosphere of nitrogen in an oil-bath pre-heated to ca 200° C. After ca 45 to 50 min the deep yellow residue was allowed to cool, and was then dissolved in hexane:ethyl acetate=4:1 and applied to a column of Merck Kieselgel 60, 230–400 mesh silica (20 g). Elution of the column with the same solvent system afforded the title compound as a white foam (56 mg) $[\alpha]_D^{21}$ +113° (c, 0.3, CHCl$_3$), $\lambda_{max}^{EtOH}$ 245 nm ($\epsilon_{max}$ 30,000); $\nu_{max}$ (CHBr$_3$) 3460 (broad OH), 1235, 1730 and 1710 cm$^{-1}$ (ester); $\delta$(CDCl$_3$) include 0.84 (d, 6 Hz; 3H), 0.96 (d, 6 Hz; 3H), 0.99 (d, 7 Hz; 3H), 1.02 (d, 6 Hz; 3H), 1.52 (s; 3H), 1.66 (s; 3H), 1.74 (s; 3H), 2.15 (s; 3H) 3.33

(m; 1H), 3.71 (d, 10 Hz; 1H), 3.90 (s; 1H), 4.06 (d, 6 Hz; 1H), 5.52 (m; 2H) 5.56 (dd, 10 and 2 Hz; 1H). m/z=636 (M+).

EXAMPLE 3

5-Acetoxy,23-desoxy $\Delta^{23}$ Factor A

Burgess' reagent ($Et_3NSO_2NCO_2Me$) (109 mg, 0.46 mmol) was added to a stirred solution of the product of Preparation 1 (299 mg) in dry toluene (10 ml) under an atmosphere of nitrogen. After 30 min at 21° the reaction mixture was refluxed for 4 h. On cooling, the yellow solution was diluted with ethyl acetate (100 ml), washed with 2M hydrochloric acid (100 ml), saturated aqueous sodium bicarbonate (100 ml) and brine (100 ml), and dried ($Na_2SO_4$). The solvent was evaporated and the residual yellow oil purified by flash chromatography (40 g Merck Kieselgel 60, 230–400 mesh). Elution with ethyl acetate: (40–60) petroleum ether (1:4) afforded the title compound as a white foam (103 mg); $[\alpha]_D^{22}$ +105° (c 0.6, $CHCl_3$); $\lambda_{max}$ (EtOH) 245.5 nm ($\epsilon$28,400); $\nu_{max}$ ($CHBr_3$) 3500 (OH), 1732 and 1715 $cm^{-1}$ (ester; $\delta(CDCl_3)$ includes 0.96 (d,7 Hz,3H), 1.00 (d, 7 Hz,3H), 1.05 (d,6 Hz,3H), 1.47 (s, 3H), 1.49 (s, 3H), 1.53 (s, 3H), 1.76 (brs, 3H), 2.15 (s, 3H), 3.34 (m, 1H), 4.06 (d, 6 Hz, 1H), 4.14 (brs, 1H), 5.5–5.6 (m, 2H).

EXAMPLE 4

23-Desoxy $\Delta^{23}$ Factor A

Aqueous sodium hydroxide (1M; 0.3 ml) was added dropwise to a stirred suspension of the compound of Example 3 in methanol (5 ml) at 0°. After 2 h at 0°, dioxan (2 ml) was added to the heterogeneous reaction mixture to give a clear yellow solution which was stirred at 0° for a further 2 h. The reaction mixture was diluted with ethyl acetate (150 ml), washed with 0.5M hydrochloric acid, water, saturated aqueous sodium bicarbonate and brine (150 ml of each) and dried ($Na_2SO_4$). The solvent was evaporated and the residue purified by flash chromatography (35 g Merck Kieselgel 60, 230–400 mesh). Elution with ethyl acetate:(40–60) petroleum ether (1:2) afforded the title compound (138 mg), $[\alpha]_D^{22}$ +108.5° (c 0.65, $CHCl_3$); $\lambda_{max}$ (EtOH) 245 nm ($\epsilon$28,300); $\nu_{max}$ ($CHBr_3$) 3550 and 3480 (OH), 1705 $cm^{-1}$ (ester); $\delta(CDCl_3)$ includes 0.97 (d, 6 Hz, 3H), 1.01 (d, 6 Hz, 3H), 1.06 (d, 6 Hz, 3H), 1.48 (s, 3H), 1.50 (s, 3H), 1.54 (s, 3H), 1.89 (s, 3H), 3.28 (m, 1H), 3.96 (d, 6 Hz, 1H), 4.13 (brs, 1H), 4.29 (t, 7 Hz, 1H).

EXAMPLE 5

5-Acetoxy,23-desoxy $\Delta^{23}$ Factor A

A solution of the product of Preparation 1 (340 mg) in dry dichloromethane (15 ml) was added dropwise over 15 minutes to a vigorously stirred solution of diethylaminosulphurtrifluoride (0.11 ml) in dry dichloromethane (10 ml) cooled to −70°. After 7 hours the cold solution was poured into a mixture of ice and solid sodium hydrogen carbonate. The mixture was allowed to warm to room temperature and the aqueous phase was separated and then was extracted with dichloromethane (2×50 ml). The combined organic phases were washed with brine, then dried and the solvent was evaporated. The residue was chromatographed on silica using hexane (60°–80°):ethyl acetate 4:1 as eluent to give the title compound (98 mg). $[\alpha]_D^{22}$ +74° (c=0.57; $CHCl_3$); $\lambda_{max}^{CHCl_3}$ 246.5 nm ($\epsilon$=22,800); m/z=636 (M+).

EXAMPLE 6

5-Acetoxy,23-desoxy $\Delta^{22}$ Factor A

A solution of the product of Preparation 4 (500 mg) in dry 2-methoxyethyl ether (diglyme) (50 ml), under a nitrogen atmosphere, was immersed in an oil-bath preheated to ca 200°. After 8¾ h at reflux, the pale yellow solution was cooled and partitioned between ethyl acetate:water (1:1, 400 ml). Repeated washing of the organic extract with water followed by a single brine wash, afforded after drying and evaporation of the organic phase, a yellow gum (545 mg). Alternatively diglyme was removed by evaporation in vacuo, followed by sequential washing of an ethyl acetate solution of the resulting oily residue, with water, aqueous sodium bicarbonate and brine. In either case the product so obtained was applied, as a solution in hexane:ethyl acetate=4:1 to a column of Merck Kieselgel 60, 230–400 mesh silica (200 g). Elution of this column with the same solvent system, under medium nitrogen pressure gave the title compound as a white foam spectroscopically similar to the sample prepared in Example 2.

EXAMPLE 7

5-Acetoxy,23-desoxy $\Delta^{22}$ Factor A

A solution of the product of Preparation 5 (1.00 g) in dry diglyme (75 ml) was heated at reflux for 17 h under an atmosphere of nitrogen. On cooling the majority of the diglyme was removed by evaporation (bath temp 50°/1 mm Hg) and the residue dissolved in ethyl acetate (250 ml). The organic solution was washed with saturated sodium bicarbonate solution water and brine and dried ($Na_2SO_4$). The solvent was evaporated and the residue purified by flash chromatography (100 g silica gel, Merck 9385). Elution with ethyl acetate:light petroleum (1:4) afforded the title compound (730 mg) as a white foam, spectroscopically identical with the sample prepared in Example 2.

The following are examples of formulations according to the invention. The term 'Active Ingredient' as used hereinafter means a compound of the invention and may be for example the compounds of Examples 1, 2, 3 or 4.

| Multidose parenteral injection | | |
|---|---|---|
| | % w/v | Range w/v |
| Active Ingredient | 4.0 | 0.1–7.5% |
| Benzyl alcohol | 2.0 | |
| Glyceryl triacetate | 30.0 | |
| Propylene glycol | to 100.0 | |

Dissolve the active ingredient in the benzyl alcohol and glyceryl triacetate. Add propylene glycol and make up to volume. Sterilize the product by conventional pharmaceutical methods, for example sterile filtration or by heating in an autoclave and package aseptically.

| Tablet Method of manufacture - wet granulation | |
|---|---|
| | mg |
| Active Ingredient | 250.0 |
| Magnesium stearate | 4.5 |
| Maize starch | 22.5 |
| Sodium starch glycolate | 9.0 |
| Sodium lauryl sulphate | 4.5 |

-continued

Tablet
Method of manufacture - wet granulation

| | mg |
|---|---|
| Microcrystalline cellulose | to tablet core weight of 450 mg |

Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Emulsifiable Concentrate | |
|---|---|
| Active ingredient | 50 g |
| Anionic emulsifier | 40 g |
| (e.g. Phenyl sulphonate CALX) | |
| Non-ionic emulsifier | 60 g |
| (e.g. Syperonic NP13) | |
| Aromatic solvent (e.g. Solvesso 100) to 1 liter. | |
| Mix all ingredients, stir until dissolved. | |
| Granules | |
| (a) Active ingredient | 50 g |
| Wood resin | 40 g |
| Gypsum granules (20–60 mesh) | to 1 kg |
| (e.g. Agsorb 100A) | |
| (b) Active ingredient | 50 g |
| Syperonic NP13 | 40 g |
| Gypsum granules (20–60 mesh) | to 1 kg. |

Dissolve all ingredients in a volatile solvent e.g. methylene chloride, add to granules tumbling in mixer. Dry to remove solvent.

We claim:

1. A compound of formula (I)

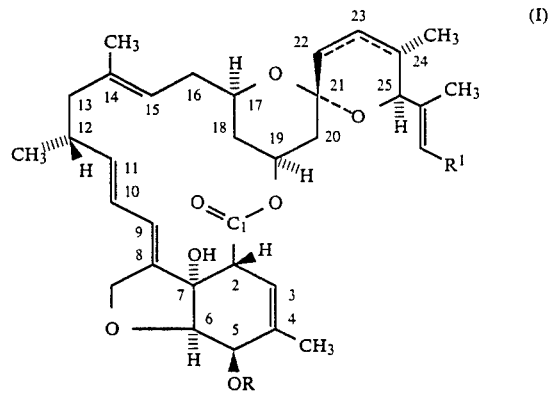

wherein OR is a hydroxyl group or a substituted hydroxyl group $-OCOR^2$, $-OCO_2R^2$ where $R^2$ is $C_{1-8}$ alkyl, $C_{1-8}$ alkyl substituted by one or more halo, carboxy, $C_{1-4}$ alkoxy, phenoxy or silyloxy substituents; $C_{2-8}$ alkenyl $C_{2-8}$ alkynyl; $C_{3-12}$ cycloalkyl; phenylalkyl in which the alkyl portion has 1–6 carbon atoms or phenyl; a formyloxy group; a group $-OR^3$ where $R^3$ is as defined above for $R^2$; a group $-OSO_2R^4$ where $R^4$ is a $C_{1-4}$ alkyl or phenyl; a silyloxy group; a $C_{5-7}$ cyclic or a tetrahydropyranyloxy group, a group $-OCO(CH_2)_n CO_2R^5$ where $R^5$ is a hydrogen atom or a group as defined for $R^2$ above and n represents zero, 1 or 2; or a group $OCONR^6R^7$ where $R^6$ and $R^7$ independently represent a hydrogen atom or a $C_{1-4}$ alkyl group; $R^1$ represents a methyl, ethyl or isopropyl group and the broken line represents a double bond at the 22,23-position or at the 23,24-position.

2. A compound according to claim 1 in which OR is a methoxycarbonyloxy, acetoxy or hydroxyl group.

3. A compound according to claim 1 in which OR is a hydroxyl group.

4. A compound according to claim 1 in which $R^1$ is an isopropyl group.

5. A compound according to claim 1 having a double bond at the 22,23-position.

6. The compound according to claim 1 in which $R^1$ is an isopropyl group, OR is a hydroxyl group and a double bond is present at the 22,23-position.

7. A pharmaceutical composition for administration to a human or animal subject containing an antibiotic effective amount of at least one compound as claimed in claim 1 together with an acceptable carrier.

8. A pesticidal composition for eradication of insect, acarine or nematode pests, containing a pesticidal effective amount of at least one compound as claimed in claim 1 and a pesticidally acceptable carrier.

* * * * *